United States Patent [19]

Eisenberg et al.

[11] Patent Number: 4,859,586
[45] Date of Patent: Aug. 22, 1989

[54] DEVICE FOR CULTIVATING BACTERIA

[76] Inventors: Eliahu Eisenberg, Remez Street 30, Tel Aviv; Reuven Padova, Kiryat Shmona Street, 11, Holon; Avner Shenfeld, Hess Street, 16; Tsvi Hirshfeld, Ben Yehuda Street, 19, both of Rehovot; Jacob Stein, Omri Street, 18a, Tel Aviv, all of Israel

[21] Appl. No.: 898,654

[22] Filed: Aug. 21, 1986

[30] Foreign Application Priority Data

Aug. 26, 1985 [IL] Israel ............................................ 76189

[51] Int. Cl.⁴ .......................... C12Q 1/04; C12Q 1/24; C12M 1/24; C12M 1/18
[52] U.S. Cl. ..................................... 435/34; 435/296; 435/300; 435/30
[58] Field of Search .................... 435/30, 34, 292, 293, 435/294, 296, 299, 300, 301, 810

[56] References Cited

U.S. PATENT DOCUMENTS 3,589,983 6/1971 Holderith et al. ............... 435/300 X
3,616,265 10/1971 Calabrese ........................ 435/293 X
3,651,926 3/1972 Elfast, Jr. ............................ 206/456
4,121,976 10/1978 Gleeson .......................... 435/296 X
4,308,347 12/1981 Forrer et al. .................... 435/300 X
4,640,895 2/1987 Davis .............................. 435/300 X
4,678,753 7/1987 Hempel et al. ...................... 435/296

FOREIGN PATENT DOCUMENTS 1310664 10/1961 France .

*Primary Examiner*—Robert J. Warden
*Assistant Examiner*—Randall E. Deck
*Attorney, Agent, or Firm*—Browdy and Neimark

[57] ABSTRACT

There is provided a hermetically closed culture vessel in which miroorganisms are cultivated simultaneously or consecutively on a liquid culture medium and on one or more solid culture media.

The culture vessel is transparent, and contains in its lower part a liquid culture medium. From the cap, closing the vessel, there extends downwardly an elongated support for the solid culture medium or media, which is essentially parallel with the central axis of the vessel, which terminates above the liquid culture medium.

The growth on the solid culture medium is conveniently inspected from the side of the culture vessel.

8 Claims, 2 Drawing Sheets

DEVICE FOR CULTIVATING BACTERIA

FIELD OF THE INVENTION

The invention relates to a culture vessel for cultivating microorganisms on two separate culture media. The invention further relates to a culture vessel for cultivating microorganisms on a liquid medium and on a solid one. The invention further relates to an integrated sterile system comprising a solid and a liquid culture medium. The invention further provides a method for the incubation of a sample to be examined simultaneously in a liquid culture medium, and on a solid culture medium, said incubation being effected in a closed integral sterile system.

BACKGROUND OF THE INVENTION

The advantages of cultivating microorganisms first on a liquid, and subsequently on a solid medium have been recognized in the art. Various devices have been proposed, and these may be divided into two basic systems:

a. A one-component system as set out in French Pat. No. 2 381 103 of Institut Pasteur, filed Feb. 18, 1977. This provides a receipient for the simultaneous biological culture on a liquid and a solid medium, where there is provided a container with a liquid medium at the lower part of the container, and with a solid medium in the throat-section of a screw-thread closure member closing the neck portion of the container.

This system has the drawback of restricted visibility of the solid culture medium, and it is possible to use one solid culture medium only. Furthermore, the system is intended for sterilization by autoclaving, and aseptic assembly.

b. A two-component system, where in one container there is provided a liquid culture medium, in a second container a slide-support of a solid culture medium, the incubation being effected in the first stage in the liquid medium; the containers are attached with each other, the solid medium is contacted with the liquid one, and the incubation is continued on the solid medium.

The two-component system has the serious drawback of possible contamination during the phase of opening the first container and attachment of the second one.

Furthermore, the solid medium is stored and transported in a separate container, and is apt to deteriorate by partial drying out. In the two-component system which is commercially available there exists also the problem of fogging of the neck-section after removal from the incubator, which has been reported in literature to cause problems.

The drawbacks of the known twin-culture media systems has been overcome to a large extent by the novel system of the invention, which has considerable advantages over the existing ones. By making use of special culture media which can be sterilized by gamma-radiation, the necessity of autoclaving is also obviated, resulting in an optimum culture system.

SUMMARY OF THE INVENTION

According to the invention there is provided an integrated single-vessel culturing system with a liquid and a solid culture medium. The system can be used with a liquid medium and with a single solid medium or with a plurality of such solid media on a plurality of support surfaces.

The solid (or semi-solid) culture medium or media are supported by an elongated carrier, which can be subdivided into a number of support sections for a plurality of culture media.

The container is advantageously wide-necked, and the closure member supports the carrier of the solid medium or media. In the vessel there is provided at its lower part the liquid medium, which reaches a level below the lower edge of the solid medium support.

According to a preferred embodiment of the invention, the entire system is sterilized by gamma-radiation, thus obviating the necessity of autoclaving. For this purpose there are advantageously used culture media as described and claimed in British Pat. No. 1 478 238 which can be sterilized by gamma radiation.

The liquid culture medium is introduced into the vessel, the closure member which carries the support of the solid culture medium is inserted (with the culture medium or media in place) and tightly closed. After sterilization the system is ready for used. It can be stored for periods in excess of 6 months without deterioration. Storage is of course in an upright position, so that the liquid medium is separate from the solid one.

When microorganisms are to be determined, blood or any other specimen is introduced into the vessel by means of a syringe needle via the resilient gasket or septum in the closure member, it is distributed in the liquid medium and incubated in this for an adequate period of time (between a few and up to about 24 hours). The preferred period of time is generally about 6 to 8 hours. At the time the bottle is tilted and the solid medium is flushed with the liquid medium, the vessel is again positioned in an upright position and incubation is continued.

At the end of the incubation period, the surface of the solid medium is visually inspected from the outside and it is easily ascertained whether colonies of microorganisms have grown on the solid medium. The bottle is so designed that in case of fogging or condensation of the bottle interior surface which may interfere with the inspection, the bottle can be tilted slightly and the condensation washed off by the broth so that the liquid does not touch the agar surface. If so, the vessel can be opened and the bacteria removed for further conventional examinations.

The support of the culture medium or media is located at the center of the vessel, and thus visiblity is very good. As the vessel is a wide one, it is possible to rinse the walls with the liquid medium if fogging occurs, and this without contacting the solid medium with such liquid.

The single-vessel system system eliminates the danger of contamination at the end of the incubation in the liquid medium. It has been found that the novel system can be used with a variety of culture media, such as, for example:

a. Modified tryptic soy broth/modified tryptic soy agar;

b. Modified Columbia broth/modified Columbia agar;

c. Modified Brain heart infusion broth/modified brain heart infusion agar;

d. Modified tryptic soy broth/modified chocolate agar.

These are used for aerobic cultures, and in this case the culture vessel is advantageously provided (prior to sterilization) with a suitable gaseous atmosphere containing an adequate quantity of carbon dioxide.

Examples of culture media for anaerobic identifications are:
 a. Modified supplement brain heart infusion broth-/modified supplement brain heart infusion agar;
 b. Modified supplement brain heart infusion broth-/modified chocolate agar;

There can also be used other nutrient media, and reference is made, for example to said British patent dealing with the production of gamma-sterilized media.

All the media stand up to the damaging effects of gamma-radiation of up to at least 3.5 Mrad and this ensures the complete sterilization of the interior of the culture system. Numerous tests were carried out and there were no false positives: the integrated one-vessel bi-phasic media system prevents the danger of contamination which is apt to occur with two-vessel systems.

The modified media set out above support the growth of even 0.1 colony forming units (C.F.U.) per ml and it is possible to attain a growth of anaerobic bacteria on the surface of the solid phase nutrient medium which is as good as can be obtained under strict anaerobic conditions on petri dishes.

In the case of both aerobic and anaerobic media, a suitable gaseous medium (which generally consists of air enriched with about 10% carbon dioxide for aerobic media and nitrogen with about 10% carbon dioxide for anaerobic media is introduced into the flask prior to sterilization.

These results are superior to those attainable hitherto in biphase culture systems.

Tests have been carried out with a wide range of microorganisms, and satisfactory results have been obtained with practically no false positives. This applies also to the cultivation of anaerobic microorganisms which can grow to visible colonies on the solid phase. It is possible to provide two different solid culture media on opposite sides of the support member. If this is of a triangular or square shape, 3 or 4 media can be used simultaneously. In most cases the culture media used (liquid and solid) are the same or similar.

The invention is described by way of illustration only with reference to the enclosed schematical drawings, which are not according to scale, and in which.

Figure 1:
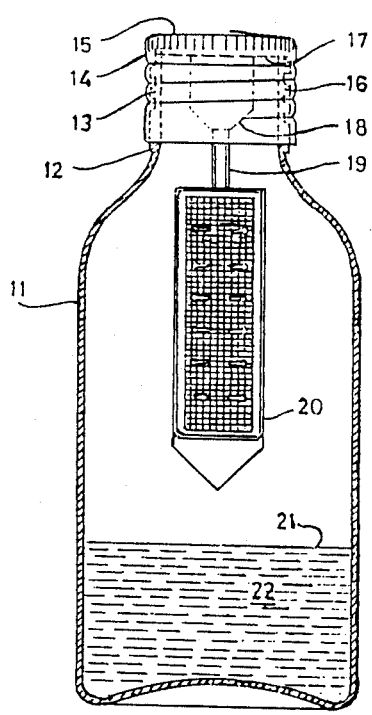
FIG. 1 is a partial longitudinal section of a culture vessel according to the invention.
Figure 2:
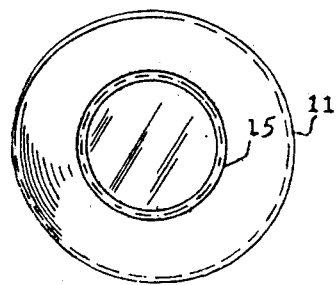
FIG. 2 is a cross-sectional view of the device of FIG. 1.

As shown in FIGS. 1 and 2, the culture system comprises a transparent vessel 11, provided with a wide neck section 12 provided with an external thread 13, and with a closure member 14 which consists of a cap 15 with an internal screw-thread 16, and into which there tightly fits the gasket or septum 17, made of a resilient material, such as rubber or suitable plastic which abuts the upper end of the neck of the flask and provides a hermetic closure. It has a downwardly extending central section 18, which supports the rod 19 to which is attached the elongated support 20 of the solid culture medium. This has a circumferential rim, thus resulting in a dish-shaped configuration, into which there can be poured the nutrient medium which solidifies in said support member. This support can have a similar shape at its rear surface, and this can be used for the same nutrient medium or for a different one. The exposed outer surface of the support having the medium thereon may be paddle-shaped having rectangular horizontal and vertical cross-sections and has a distinct nutrient medium on each vertical outer surface thereof.

As shown, the vessel is intended to be filled up to level 21 with a liquid nutrient medium 22, there being adequate space between the upper surface of the liquid and the lower end of the support of the solid culture medium. In a vessel of about 55 mm diameter and of about 120 mm height, a quantity of about 50 ml liquid culture medium is satisfactory. In this case a cap of about 30 mm diameter was used. It is clear that the dimensions are by way of illustration only.

Figure 3:
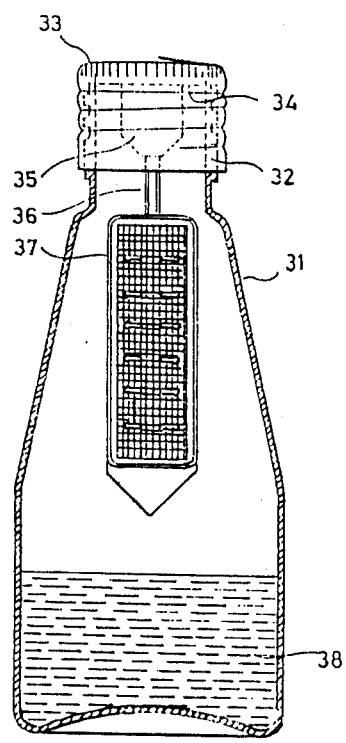
FIG. 3 is a partial longitudinal section through another type of vessel according to the invention.

A similar culture system is illustrated in FIG. 3 which comprises a conical transparent vessel 31 (glass or plastic), with a wide neck section 32, there being provided a closure member 33 with an internal gasket or septum 34 with downward extending base 35 holding via rod 36 the paddle-like support member 37 of the culture medium. The support is advantageously made of an insert plastic material. This may be provided with a surface treated in such manner as to provide better adherence of the culture medium. Also in this embodiment, the liquid nutrient medium 38 is filled up to a level well below the lower end of the support member 37. The system is used in the same manner as the one set out in FIG. 1 and 2.

The culture media are introduced into the vessel and into the support, where the solid medium is allowed to solidify while this is in a horizontal position. Before assembly and tight closure, the gaseous atmosphere in the vessel is adjusted to the intended use and the system is sterilized in an upright position by an ionizing irradiation, preferably gamma-irradiation.

After introduction of the sample by a syringe needle via the gasket or septum 34, the liquid medium is mixed with the sample. This may be a quantity of a few millimeters of blood or other fluid. After incubation, for about 4 to 8 hours, the liquid medium is inspected for any changes (color, consistency, gas evolution), and the solid nutrient medium is flushed with the liquid and incubation is continued. The solid medium may be contacted at predetermined intervals with said liquid medium. After a predetermined period of time the solid culture medium is visually inspected and colonies can be removed for further conventional evaluation, such as identification of the cultured microorganisms. The novel system can be used for a wide variety of uses: it is suitable for blood cultures or for cultures of other physiological fluids; it can be used for ascertaining the sterility of solutions intended for injection, such as infusion solutions, feeding solutions, dialysis solutions, water and other environmental tests, and for the testing of sterility of pharmaceutical and food products, etc. The sterilized system has an adequate shelf-life without any apparent deterioration of loss of efficiency. Such systems can be provided in a wide variety of shapes and sizes, depending on the intended use. The above description is by way of illustration only and it is clear that modifications in the shape and size and arrangement of parts may be resorted to without departing from the present invention.

Another embodiment of a culture system according to the invention is illustrated with reference to FIG. 5 (and FIG. 5a which is a sectional view through the device of FIG. 5).

Figure 5:
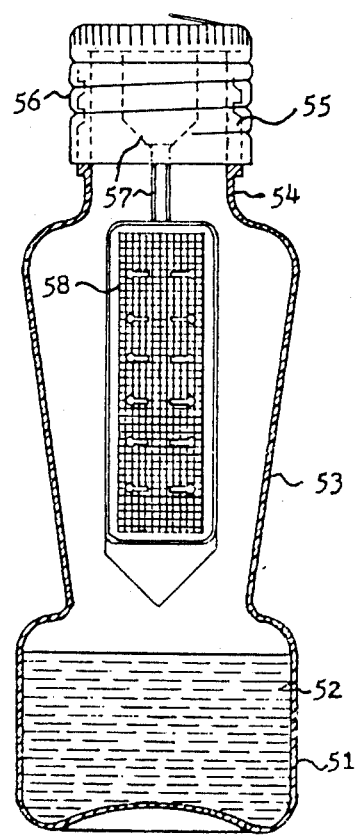
FIG. 5 is a view of another vessel according to the invention.
Figure 5A:
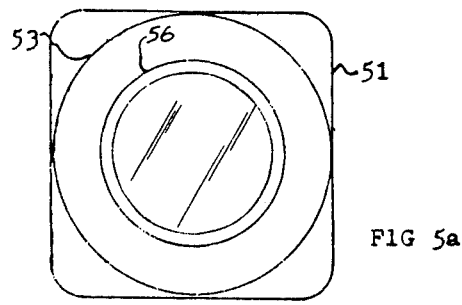

The device illustrated in FIG. 5 comprises a plastic bottle having a square bottom section 51, in which there is provided the liquid culture medium 52, and a conical upper part 53 which merges into a neck section 54 which is provided with an external screw-thread 55 on which there is mounted the cap 56, which is provided with an internal gasket or septum, not shown, which provides a hermetic seal between the cap 56 and the neck-section 54.

Figure 4:
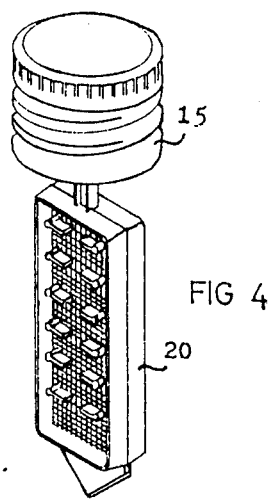
FIG. 4 is a perspective view of a support member for 2 identical or different culture media.

From said gasket or septum there extends downwardly a support member 57, to which there is attached the rectangular member 58, which is of the type illustrated in FIG. 4, and which advantageously supports on each of its two faces a different solid culture medium. As is apparent from the figure, the member 58 extends deep into the conical part 53, and terminates above the level of the liquid culture medium 52. The culture system is prepared as set out above with reference to the preceding figures, and there is established in same a desired gaseous atmosphere. After sterilization, preferably by gamma radiation, the culture system is ready for use.

After incubation, there generally form droplets on the side walls which impair visual inspection of the growth on the solid culture medium. Due to the slanting side-wall of the conical section it is possible to tilt the vessel and to rinse the side walls with the liquid culture medium without same touching the solid culture medium.

We claim:

1. An integral sterile closed device for simultaneous cultivation of microorganisms on a solid and on a liquid nutrient medium, comprising a transparent vessel with an elongated upper section with side walls and a lower part, a liquid nutrient medium within said lower section, the lower part being of a larger diameter than said upper section, said upper section is of a conical, downwardly and inwardly tapering shape so as to permit tilting of the vessel to rinse the side walls of the upper section with the liquid medium in the vessel and thereby remove droplets adhering to the upper section after cultivation, without contact of the solid medium by liquid medium in the vessel, and said upper section also being provided at its uppermost part with a closure cap and a hermetically sealing resilient septum in the upper part of said cap, a rod downwardly depending from said septum, an elongated downwardly extending support means having a solid nutrient medium on an exposed vertical outer surface thereof, said support means being attached to said rod and essentially parallel with a central axis of the vessel, a lower end of said support means terminating above an uppermost surface of said liquid nutrient medium when said vessel is upright, said cap having an opening where the sample may be introduced into said vessel by inserting a syringe needle through the septum.

2. A culture device according to claim 1, where the upper section includes an upper neck portion and a lower bottom portion which is wider than the upper neck portion.

3. A device according to claim 2, which has been sterilized by ionizing irradiation and wherein said solid and liquid media are suitable for sterilization by ionizing irradiation.

4. A culture system according to claim 1, where the exposed outer surface having the solid medium thereon has rectangular horizontal and vertical cross-sections and has a distinct solid nutrient medium on each vertical outer surface thereof.

5. A device according to claim 1, which contains a gaseous medium selected for growth of aerobic microorganisms.

6. A device according to claim 1, which contains a gaseous medium selected for growth of anaerobic microorganisms.

7. A method for determining the presence of and for identifying microorganisms in a liquid, which comprises:

(a) inoculating a sample of a liquid, using a syringe, through a septum of a closed culture device including a transparent vessel with an elongated upper section with side walls and a lower part, which lower part defines containing means containing a liquid nutrient medium, the lower part being of a larger diameter than said upper section, said upper section is of a conical, downwardly and inwardly tapering shape so as to permit tilting of the vessel to rinse the side walls of the upper section with the liquid medium in the vessel and thereby remove droplets adhering to the upper section after cultivation, without contact of the solid medium by liquid medium in the vessel, and said upper section also being provided at its uppermost part with a closure cap and a hermetically sealing resilient septum in the upper part of said cap, a rod downwardly depending from said septum, an elongated downwardly extending support means supporting a solid nutrient medium on an exposed vertical surface thereof, said support means being attached to said rod and essentially parallel with a central axis of the vessel, a lower end of said support means terminating above an upper surface of said liquid nutrient medium, said cap having an opening where the sample may be introduced into said vessel by inserting a syringe needle through the septum;

(b) contacting the sample with the liquid nutrient medium and dispersing it in same;

(c) incubating the inoculated liquid nutrient medium in said closed device for a first predetermined period of time;

(d) contacting the solid nutrient medium with the incubated liquid nutrient medium located in the same closed device; then, (e) incubating said solid nutrient medium for a second predetermined period of time;

(f) determining after this second period of time whether colonies are present on the solid nutrient medium;

(g) opening said vessel; and, (h) identifying any microorganisms present on the solid nutrient medium, steps (a)-(f) being performed without opening said closed device.

8. A method according to claim 7, where the solid nutrient medium is contacted repeatedly with the liquid nutrient medium during the second incubation period of the solid medium.

* * * * *